(12) United States Patent
Dubois et al.

(10) Patent No.: US 8,481,745 B2
(45) Date of Patent: Jul. 9, 2013

(54) N-(AMINOHETEROARYL)-1H-INDOLE-2-CARBOXAMIDE DERIVATIVES, PREPARATION THEREOF AND THERAPEUTIC USE THEROF

(75) Inventors: Laurent Dubois, Le Plessis-Robinson (FR); Yannick Evanno, Dannemois (FR); Andre Malanda, Villejust (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/530,261

(22) Filed: Jun. 22, 2012

(65) Prior Publication Data

US 2012/0264944 A1 Oct. 18, 2012

Related U.S. Application Data

(60) Division of application No. 12/358,639, filed on Jan. 23, 2009, now Pat. No. 8,227,489, which is a continuation of application No. PCT/FR2007/001250, filed on Jul. 20, 2007.

(30) Foreign Application Priority Data

Jul. 24, 2006 (FR) ..................... 06 06742

(51) Int. Cl.
C07D 213/74 (2006.01)

(52) U.S. Cl.
USPC ........................................ 546/307

(58) Field of Classification Search
None
See application file for complete search history.

(56) References Cited

U.S. PATENT DOCUMENTS 7,045,544 B2   5/2006   Erguden et al.

FOREIGN PATENT DOCUMENTS

| GB | 870027 | 6/1961 | |
|---|---|---|---|
| JP | 54028330 | * | 3/1979 |
| WO | WO0248152 | | 6/2002 |
| WO | WO2004052869 | | 6/2004 |
| WO | WO2004062655 | | 7/2004 |
| WO | WO2004110985 | | 12/2004 |
| WO | WO2005028452 | | 3/2005 |
| WO | WO2005028455 | | 3/2005 |
| WO | WO2005035526 | | 4/2005 |
| WO | WO2006072736 | | 7/2006 |
| WO | WO2007011284 | | 1/2007 |
| WO | WO2007060140 | | 5/2007 |
| WO | WO2006040522 | | 6/2012 |

OTHER PUBLICATIONS

Chemical Abstracts 91:40904 which is JP 54028330, Koei Chemical Co., Ltd, Mar. 1979.*
Translation of JP 54028330, Koei Chemical Co., Ltd, Mar. 1979.*
Brands, M., et al., Novel, Selective Indole-Based ECE Inhibitors: Lead Orientation Via Solid-Phase and Classical Synthesis, Biorganic & Medicinal Chemistry Letter, col. 15, (2005), pp. 4201-4205.
Hurst, Derek, T., et al. The Synthesis of Some 2-(Substituted) 5-Nitropyrimidines, Heterocycles, vol. 6, No. 12, (1977) pp. 1999-2004.
16. Fox, G.J., et al. Bromination of 3-Amino- and 2-Dimethylamino-Pyridine, J. Chem Soc. Perkin Trans 1, (1973), vol. 1, pp. 68-69.

* cited by examiner

*Primary Examiner* — Zinna Northington Davis
(74) *Attorney, Agent, or Firm* — Scully, Scott, Murphy & Presser, P.C.

(57) ABSTRACT

The invention relates to compounds of general formula (I):

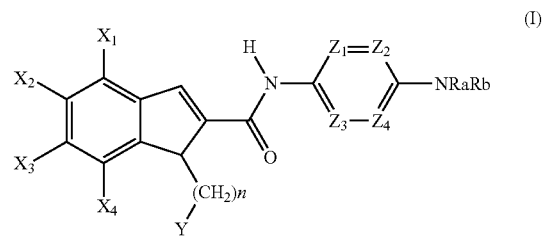

Wherein n, $X_1$, $X_2$, $X_3$, $X_4$, Y, $Z_1$, $Z_2$, $Z_3$, $Z_4$, Ra and Rb are as defined herein. The invention also relates to process for the preparation of compounds of formula (I) and their therapeutic use.

1 Claim, No Drawings

N-(AMINOHETEROARYL)-1H-INDOLE-2-CARBOXAMIDE DERIVATIVES, PREPARATION THEREOF AND THERAPEUTIC USE THEROF

CROSS REFERENCE TO RELATED APPLICATIONS

The present application is a divisional of U.S. Ser. No. 12/358,639 filed Jan. 23, 2009 now U.S. Pat. No. 8,227,489, which is a continuation of PCT/FR2007/001250, filed Jul. 20, 2007

A subject matter of the invention is N-(aminoheteroaryl)-1H-indole-2-carboxamide derivatives which exhibit an in vitro and in vivo antagonist activity for receptors of TRPV1 (or VR1) type.

A first subject matter of the invention is the compounds corresponding to the general formula (I) below.

Another subject matter of the invention is processes for the preparation of the compounds of general formula (I).

Another subject matter of the invention is the use of the compounds of general formula (I) in particular in medicaments or in pharmaceutical compositions.

The compounds of the invention correspond to the general formula (I):

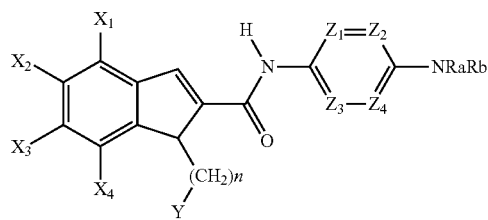

in which:

$X_1$ represents a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_8$-fluoroalkyl, cyano, C(O)$NR_1R_2$, nitro, $C_1$-$C_6$-thioalkyl, —S(O)—$C_1$-$C_6$-alkyl, —S(O)$_2$—$C_1$-$C_6$-alkyl, SO$_2$$NR_1R_2$, aryl-$C_1$-$C_6$-alkylene, aryl or heteroaryl group, the aryl and heteroaryl optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$X_2$ represents a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_7$-alkoxyl, $C_3$-$C_7$-cycloalkyl-$C_1$-$C_6$-alkylene-O—, $C_1$-$C_6$-fluoroalkoxyl, cyano, C(O)$NR_1R_2$, $C_1$-$C_6$-thioalkyl, —S(O)—$C_1$-$C_6$-alkyl, —S(O)$_2$—$C_1$-$C_6$-alkyl, SO$_2$$NR_1R_2$, aryl-$C_1$-$C_6$-alkylene, aryl or heteroaryl, the aryl and heteroaryl optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$X_3$ and $X_4$ represent, independently of one another, a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, cyano, C(O)$NR_1R_2$, nitro, $NR_1R_2$, $C_1$-$C_6$-thioalkyl, —S(O)—$C_1$-$C_6$-alkyl, —S(O)$_2$—$C_1$-$C_6$-alkyl, SO$_2$$NR_1R_2$, $NR_3COR_4$, $NR_3SO_2R_5$, aryl-$C_1$-$C_6$-alkylene, aryl or heteroaryl group, the aryl and heteroaryl optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$Z_1$, $Z_2$, $Z_3$ and $Z_4$ represent, independently of one another, a nitrogen atom or a C($R_6$) group, at least one corresponding to a nitrogen atom and at least one corresponding to a C($R_6$) group; the nitrogen atom or one of the nitrogen atoms present in the ring, defined as nitrogen of position 1, optionally being substituted by $R_7$ when the carbon atom in the 2 or 4 position with respect to this reference nitrogen is substituted by an oxo or thio group;

n is equal to 0, 1, 2 or 3;

Y represents an aryl or a heteroaryl optionally substituted by one or more groups chosen from a halogen atom or a $C_1$-$C_6$-alkyl, $C_3$-$C_6$-cycloalkyl, $C_3$-$C_7$-cycloalkyl-$C_1$-$C_3$-alkylene, $C_1$-$C_8$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, cyano, C(O)$NR_1R_2$, nitro, $NR_1R_2$, $C_1$-$C_6$-thioalkyl, thiol, —S(O)—$C_1$-$C_6$-alkyl, —S(O)$_2$—$C_1$-$C_6$-alkyl, SO$_2$$NR_1R_2$, $NR_3COR_4$, $NR_3SO_2R_5$, aryl-$C_1$-$C_6$-alkylene or aryl group, the aryl and the aryl-$C_1$-$C_6$-alkylene optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

Ra and Rb represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxyl, $C_3$-$C_7$-cycloalkyl-$C_1$-$C_6$-alkylene-O—, $C_1$-$C_6$-fluoroalkoxyl, aryl or heteroaryl group, it being possible for Ra and Rb optionally to be substituted by one or more Rc groups which are identical to or different from one another;

Rc represents a halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, cyano, C(O)$NR_1R_2$, $NR_1R_2$, SO$_2$$NR_1R_2$, $NR_3COR_4$, $NR_3SO_2R_5$, OC(O)$NR_1R_2$, $NR_3COOR_4$, $NR_3CONR_1R_2$, hydroxyl, thiol, oxo, thio, aryl-$C_1$-$C_6$-alkylene, aryl or heteroaryl group, the aryl and the heteroaryl optionally being substituted by one or more substituents chosen from a halogen or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_1$-$C_6$-fluoroalkoxyl, nitro or cyano group;

$R_1$ and $R_2$ represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene or aryl group; or $R_1$ and $R_2$ together form, with the nitrogen atom which carries them, an azetidinyl, pyrrolidinyl, piperidinyl, azepinyl, morpholinyl, thiomorpholinyl, piperazinyl or homopiperazinyl group, this group optionally being substituted by a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_3$ and $R_4$ represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_5$ represents a $C_1$-$C_6$-alkyl, $C_3$-$C_7$-cycloalkyl, $C_3$-$C_7$-cycloalkyl-$C_1$-$C_3$-alkylene, aryl-$C_1$-$C_6$-alkylene, aryl or heteroaryl group;

$R_6$ represents a hydrogen or halogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, $C_1$-$C_6$-thioalkyl, —S(O)—$C_1$-$C_6$-alkyl, —S(O)$_2$—$C_1$-$C_6$-alkyl, aryl, aryl-$C_1$-$C_6$-alkylene, heteroaryl, hydroxyl, thiol, oxo or thio group;

$R_7$ represents a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, $C_1$-$C_6$-alkoxyl, $C_3$-$C_7$-cycloalkyl-$C_1$-$C_6$-alkylene-O—, $C_1$-$C_6$-fluoroalkoxyl, aryl, aryl-$C_1$-$C_6$-alkylene or heteroaryl group.

In the compounds of general formula (I), the nitrogen atom or atoms can be in the oxidized (N-oxide) form.

Among the compounds of general formula (I) which are subject matters of the invention, a first subgroup of compounds is composed of the compounds for which $X_1$, $X_2$, $X_3$ and $X_4$ are chosen, independently of one another, from a hydrogen or halogen atom or a $C_1$-$C_6$-alkyl or $C_1$-$C_6$-fluoroalkyl group.

Among the compounds of general formula (I) which are subject matters of the invention, a second subgroup of compounds is composed of the compounds for which $X_1$, $X_2$, $X_3$ and $X_4$ are chosen, independently of one another, from a hydrogen or fluorine atom or a trifluoromethyl group.

Among the compounds of general formula (I) which are subject matters of the invention, a third subgroup of compounds is composed of the compounds for which $X_1$ and $X_4$ represent a hydrogen atom and $X_2$ and $X_3$ are chosen, independently of one another, from a hydrogen or halogen atom or a $C_1$-$C_6$-fluoroalkyl group.

Among the compounds of general formula (I) which are subject matters of the invention, a fourth subgroup of compounds is composed of the compounds for which $X_1$ and $X_4$ represent a hydrogen atom and $X_2$ and $X_3$ are chosen, independently of one another, from a hydrogen or fluorine atom or a trifluoromethyl group.

Among the compounds of general formula (I) which are subject matters of the invention, a fifth subgroup of compounds is composed of the compounds for which $Z_1$, $Z_2$, $Z_3$ and $Z_4$ represent, independently of one another, a nitrogen atom or a $C(R_6)$ group, at least two of them corresponding to a $C(R_6)$ group; the nitrogen atom or one of the nitrogen atoms present in the ring, defined as nitrogen of position 1, optionally being substituted by $R_7$ when the carbon atom in the 2 or 4 position with respect to this reference nitrogen is substituted by an oxo or thio group; $R_6$ and $R_7$ being as defined in the general formula (I).

Among the compounds of general formula (I) which are subject matters of the invention, a sixth subgroup of compounds is composed of the compounds for which $Z_1$ and $Z_2$ represent a $C(R_6)$ group and $Z_3$ and $Z_4$ represent a nitrogen atom, $R_6$ being as defined in the general formula (I).

Among the compounds of general formula (I) which are subject matters of the invention, a seventh subgroup of compounds is composed of the compounds for which $Z_1$ and $Z_2$ represent a $C(R_g)$ group and $Z_3$ and $Z_4$ represent a nitrogen atom, $R_6$ corresponding to a hydrogen atom.

Among the compounds of general formula (I) which are subject matters of the invention, an eighth subgroup of compounds is composed of the compounds for which $Z_1$, $Z_2$, $Z_3$ and $Z_4$ represent, independently of one another, a nitrogen atom or a $C(R_6)$ group, one corresponding to a nitrogen atom and the others corresponding to a $C(R_6)$ group; the nitrogen atom present in the ring, defined as nitrogen of position 1, optionally being substituted by $R_7$ when the carbon atom in the 2 or 4 position with respect to this reference nitrogen is substituted by an oxo or thio group; $R_6$ and $R_7$ being as defined in the general formula (I).

Among the compounds of general formula (I) which are subject matters of the invention, a ninth subgroup of compounds is composed of the compounds for which $Z_1$ and $Z_2$ represent a $C(R_6)$ group and $Z_3$ and $Z_4$ represent, independently of one another, a nitrogen atom or a $C(R_6)$ group, one of $Z_3$ and $Z_4$ corresponding to a $C(R_6)$ group; $R_6$ representing a hydrogen or halogen atom or a $C_1$-$C_6$-alkyl or $C_1$-$C_6$-fluoroalkyl group.

Among the compounds of general formula (I) which are subject matters of the invention, a tenth subgroup of compounds is composed of the compounds for which $Z_1$ and $Z_2$ represent a $C(R_6)$ group and $Z_3$ and $Z_4$ represent, independently of one another, a nitrogen atom or a $C(R_6)$ group, one of $Z_3$ and $Z_4$ corresponding to a $C(R_6)$ group; $R_6$ representing a hydrogen or fluorine atom or a methyl or trifluoromethyl group.

Among the compounds of general formula (I) which are subject matters of the invention, an eleventh subgroup of compounds is composed of the compounds for which $Z_4$ represents a nitrogen atom and $Z_1$, $Z_2$ and $Z_3$ represent, independently of one another, a $C(R_6)$ group; the nitrogen atom present in the ring, defined as nitrogen of position 1, optionally being substituted by $R_7$ when the carbon atom in the 2 or 4 position with respect to this reference nitrogen is substituted by an oxo or thio group; $R_6$ and $R_7$ being as defined in the general formula (I).

Among the compounds of general formula (I) which are subject matters of the invention, a twelfth subgroup of compounds is composed of the compounds for which $Z_4$ represents a nitrogen atom and $Z_1$, $Z_2$ and $Z_3$ represent, independently of one another, a $C(R_6)$ group, $R_6$ representing a hydrogen or halogen atom or a $C_1$-$C_6$-alkyl or $C_1$-$C_6$-fluoroalkyl group.

Among the compounds of general formula (I) which are subject matters of the invention, a thirteenth subgroup of compounds is composed of the compounds for which $Z_4$ represents a nitrogen atom and $Z_1$, $Z_2$ and $Z_3$ represent, independently of one another, a $C(R_6)$ group, $R_6$ representing a hydrogen or fluorine atom or a methyl or trifluoromethyl group.

Among the compounds of general formula (I) which are subject matters of the invention, a fourteenth subgroup of compounds is composed of the compounds for which n is equal to 1.

Among the compounds of general formula (I) which are subject matters of the invention, a fifteenth subgroup of compounds is composed of the compounds for which Y represents an aryl or heteroaryl optionally substituted by one or more halogen atoms.

Among the compounds of general formula (I) which are subject matters of the invention, a sixteenth subgroup of compounds is composed of the compounds for which Y represents a phenyl or a pyridinyl, the phenyl optionally being substituted by a halogen atom.

Among the compounds of general formula (I) which are subject matters of the invention, a seventeenth subgroup of compounds is composed of the compounds for which Ra and Rb represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_6$-fluoroalkyl, hydroxyl, $C_1$-$C_6$-alkoxyl or $C_3$-$C_7$-cycloalkyl-$C_1$-$C_6$-alkylene-O— group, it being possible for Ra and Rb to be optionally substituted by one or more Rc groups which are identical to or different from one another;

Rc represents a $C_1$-$C_6$-alkoxyl, $NH_2$ or hydroxyl group.

Among the compounds of general formula (I) which are subject matters of the invention, an eighteenth subgroup of compounds is composed of the compounds for which Ra and Rb represent, independently of one another, a hydrogen atom or a $C_1$-$C_6$-alkyl or $C_3$-$C_7$-cycloalkyl group, it being possible for Ra and Rb to be optionally substituted by one or more Rc groups which are identical to or different from one another; Rc represents an oxo group.

Among the compounds of general formula (I) which are subject matters of the invention, a nineteenth subgroup of compounds is composed of the compounds for which Ra and Rb represent, independently of one another, a hydrogen atom or a methyl, propyl or cyclopropyl group, it being possible for Ra and Rb to be optionally substituted by an Rc group where Rc represents an oxo group.

Among the compounds of general formula (I) which are subject matters of the invention, a twentieth subgroup of compounds is composed of the compounds for which $X_1$, $X_2$, $X_3$, $X_4$, $Z_1$, $Z_2$, $Z_3$, $Z_4$, n, Y, Ra and Rb are as defined in the general formula (I), provided that, when Y represents an unsubstituted phenyl, then n is equal to 2 or 3.

Among the compounds of general formula (I) which are subject matters of the invention, a twenty-first subgroup of compounds is composed of the compounds for which $X_1$, $X_2$, $X_3$, $X_4$, $Z_1$, $Z_2$, $Z_3$, $Z_4$, n, Y, Ra and Rb are as defined in the above subgroups.

Among the compounds of general formula (I) which are subject matters of the invention, a twenty-second subgroup of compounds is composed of the compounds for which $X_1$, $X_2$, $X_3$ and $X_4$ are chosen, independently of one another, from a hydrogen or halogen atom or a $C_1$-$C_6$-alkyl or $C_1$-$C_6$-fluoroalkyl group; and/or $Z_1$, $Z_2$, $Z_3$ and $Z_4$ represent, independently of one another, a nitrogen atom or a $C(R_6)$ group, one corresponding to a nitrogen atom and the others corresponding to a $C(R_6)$ group; the nitrogen atom present in the ring, defined as nitrogen of position 1, optionally being substituted by $R_7$ when the carbon atom in the 2 or 4 position with respect to this reference nitrogen is substituted by an oxo or thio group; $R_6$ and $R_7$ being as defined in the general formula (I); and/or n is equal to 1; and/or Ra and Rb represent, independently of one another, a hydrogen atom or a $C_1$-$C_6$-alkyl, $C_3$-$C_7$-cycloalkyl, $C_3$-$C_7$-cycloalkyl-$C_1$-$C_3$-alkylene, $C_1$-$C_8$-fluoroalkyl, hydroxyl, $C_1$-$C_6$-alkoxyl or $C_3$-$C_7$-cycloalkyl-$C_1$-$C_6$-alkylene-O— group, it being possible for Ra and Rb to be optionally substituted by one or more Rc groups which are identical to or different from one another;

Rc represents a $C_1$-$C_6$-alkoxyl, $NH_2$ or hydroxyl group.

Mention may be made, among the compounds of general formula (I) which are subject matters of the invention, of the following compounds:

1. N-[6-(methylamino)pyridin-3-yl]-5-fluoro-1-(3-fluorobenzyl)-1H-indole-2-carboxamide
2. N-[6-(dimethylamino)pyridin-3-yl]-5-fluoro-1-(3-fluorobenzyl)-1H-indole-2-carboxamide hydrochloride (1:1)
3. N-[6-(methylamino)pyridin-3-yl]-5-fluoro-1-benzyl-1H-indole-2-carboxamide
4. N-[6-(dimethylamino)pyridin-3-yl]-5-fluoro-1-benzyl-1H-indole-2-carboxamide
5. N-[6-(dimethylamino)pyridin-3-yl]-6-fluoro-1-(3-fluorobenzyl)-1H-indole-2-carboxamide
6. N-[5-(dimethylamino)pyridin-2-yl]-5-fluoro-1-(3-fluorobenzyl)-1H-indole-2-carboxamide
7. N-[6-(methylamino)pyridin-3-yl]-5-fluoro-1-(2-fluorobenzyl)-1H-indole-2-carboxamide
8. N-[6-(1-propylamino)pyridin-3-yl]-5-fluoro-1-(3-fluorobenzyl)-1H-indole-2-carboxamide hydrochloride (1:1)
9. N-[6-(cyclopropylamino)pyridin-3-yl]-5-fluoro-1-(3-fluorobenzyl)-1H-indole-2-carboxamide hydrochloride (1:1)
10. N-[6-(dimethylamino)pyridin-3-yl]-5-fluoro-1-(4-fluorobenzyl)-1H-indole-2-carboxamide and its hydrochloride salt (1:1)
11. N-[6-(acetylamino)pyridin-3-yl]-5-fluoro-1-(3-fluorobenzyl)-1H-indole-2-carboxamide
12. N-[6-(dimethylamino)pyridin-3-yl]-5-trifluoromethyl-1-(3-fluorobenzyl)-1H-indole-2-carboxamide
13. N-[6-dimethylamino-4-methylpyridin-3-yl]-5-fluoro-1-(3-fluorobenzyl)-1H-indole-2-carboxamide
14. N-[6-(acetylamino)pyridin-3-yl]-6-trifluoromethyl-1-(3-fluorobenzyl)-1H-indole-2-carboxamide
15. N-[6-methylamino-4-methylpyridin-3-yl]-5-fluoro-1-(3-fluorobenzyl)-1H-indole-2-carboxamide
16. N-[6-dimethylamino-5-methylpyridin-3-yl]-5-fluoro-1-(3-fluorobenzyl)-1H-indole-2-carboxamide
17. N-[6-dimethylamino-4-methylpyridin-3-yl]-5-fluoro-1-(pyridin-4-ylmethyl)-1H-indole-2-carboxamide
18. N-[6-methylamino-4-methylpyridin-3-yl]-5-fluoro-1-(pyridin-4-ylmethyl)-1H-indole-2-carboxamide
19. N-[6-dimethylamino-5-methylpyridin-3-yl]-5-fluoro-1-(pyridin-4-ylmethyl)-1H-indole-2-carboxamide
20. N-[6-dimethylamino-5-(trifluoromethyl)pyridin-3-yl]-5-fluoro-1-(3-fluorobenzyl)-1H-indole-2-carboxamide
21. N-[6-methylamino-2-methylpyridin-3-yl]-5-fluoro-1-(3-fluorobenzyl)-1H-indole-2-carboxamide
22. N-[5-(dimethylamino)pyridazin-2-yl]-5-fluoro-1-(3-fluorobenzyl)-1H-indole-2-carboxamide and its hydrochloride salt (1:1)
23. N-[5-(dimethylamino)pyridazin-2-yl]-5-trifluoromethyl-1-(3-fluorobenzyl)-1H-indole-2-carboxamide
24. N-[5-(dimethylamino)pyridazin-2-yl]-6-trifluoromethyl-1-(3-fluorobenzyl)-1H-indole-2-carboxamide
25. N-[5-(dimethylamino)pyridazin-2-yl]-5-trifluoromethyl-1-(pyridin-4-ylmethyl)-1H-indole-2-carboxamide hydrochloride (1:1)
26. N-[6-(methylamino)pyridin-3-yl]-5-fluoro-1-(pyridin-4-ylmethyl)-1H-indole-2-carboxamide
27. N-[6-dimethylamino-5-fluoropyridin-3-yl]-5-fluoro-1-(3-fluorobenzyl)-1H-indole-2-carboxamide
28. N-[6-dimethylamino-4-(trifluoromethyl)pyridin-3-yl]-5-fluoro-1-(3-fluorobenzyl)-1H-indole-2-carboxamide In the context of the present invention:

$C_t$-$C_z$ where t and z can take the values from 1 to 7 is understood to mean a carbon chain which can have from t to z carbon atoms, for example $C_1$-$C_3$ is understood to mean a carbon chain which can have from 1 to 3 carbon atoms;

an alkyl is understood to mean a saturated, linear or branched, aliphatic group. Mention may be made, by way of examples, of the methyl, ethyl, propyl, isopropyl, butyl, isobutyl, tert-butyl or pentyl groups, and the like;

an alkylene is understood to mean a saturated, linear or branched, divalent alkyl group; for example, a $C_{1-3}$-alkylene group represents a linear or branched divalent carbon chain of 1 to 3 carbon atoms, for example a methylene, ethylene, 1-methylethylene or propylene;

a cycloalkyl is understood to mean a cyclic carbon group. Mention may be made, by way of examples, of the cyclopropyl, cyclobutyl, cyclopentyl or cyclohexyl groups, and the like;

a fluoroalkyl is understood to mean an alkyl group, one or more hydrogen atoms of which have been substituted by a fluorine atom;

an alkoxy is understood to mean an —O-alkyl radical where the alkyl group is as defined above;

a fluoroalkoxy is understood to mean an alkoxy group, one or more hydrogen atoms of which have been substituted by a fluorine atom;

a thioalkyl is understood to mean an —S-alkyl radical where the alkyl group is as defined above;

an aryl is understood to mean an aromatic cyclic group comprising between 6 and 10 carbon atoms.

Mention may be made, as examples of aryl groups, of the phenyl or naphthyl groups;

a heteroaryl is understood to mean a 5- to 10-membered aromatic cyclic group comprising from 1 to 4 heteroatoms chosen from O, S or N. Mention may be made, by way of examples, of the imidazolyl, thiazolyl, oxazolyl, furanyl, thiophenyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl, benzotriazolyl, quinolinyl, isoquinolinyl or quinoxalinyl groups;

a halogen atom is understood to mean a fluorine, a chlorine, a bromine or an iodine;

"oxo" means "=O";

"thio" means "=S".

The compounds of formula (I) can comprise one or more asymmetric carbon atoms. They can thus exist in the form of enantiomers or of diastereoisomers. These enantiomers or diastereoisomers, and their mixtures, including racemic mixtures, come within the invention.

The compounds of formula (I) can exist in the form of bases or of addition salts with acids. Such addition salts come within the invention.

These salts are advantageously prepared with pharmaceutically acceptable acids but the salts of other acids, for example of use in the purification or the isolation of the compounds of formula (I), also come within the invention.

The compounds of general formula (I) can occur in the form of hydrates or of solvates, namely in the form of combinations or associations with one or more molecules of water or with a solvent. Such hydrates and solvates also come within the invention.

In what follows, the term "leaving group" is understood to mean a group which can be easily split from a molecule by cleavage of a heterolytic bond with departure of an electron pair. This group can thus be easily replaced by another group, for example during a substitution reaction. Such leaving groups are, for example, halogens or an activated hydroxyl group, such as a methanesulfonate, benzenesulfonate, p-toluenesulfonate, triflate, acetate, and the like. Examples of leaving groups and references for their preparation are given in "Advances in Organic Chemistry", J. March, 5$^{th}$ edition, Wiley Interscience, 2001.

In accordance with the invention, the compounds of general formula (I) can be prepared according to the process illustrated by the following scheme 1.

According to scheme 1, the compounds of general formula (IV) can be obtained by reaction of a compound of general formula (II), in which $X_1$, $X_2$, $X_3$ and $X_4$ are as defined in the general formula (I) and B represents a $C_1$-$C_6$-alkoxyl group, with a compound of general formula (III), in which Y and n are as defined in the general formula (I) and LG represents a leaving group where LG represents a hydroxyl group.

The compounds of general formula (II) are available commercially or are prepared according to numerous processes described in the literature (D. Knittel, *Synthesis*, 1985, 2, 186; T. M. Williams, *J. Med. Chem.*, 1993, 36(9), 1291; JP2001151771A2, for example).

Scheme 1

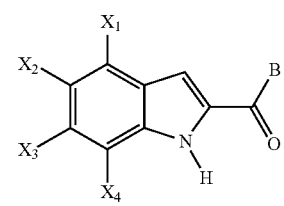

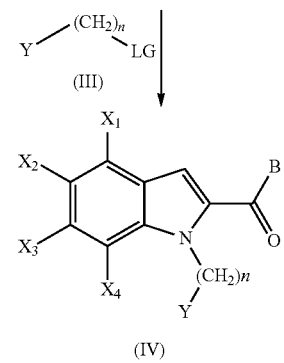

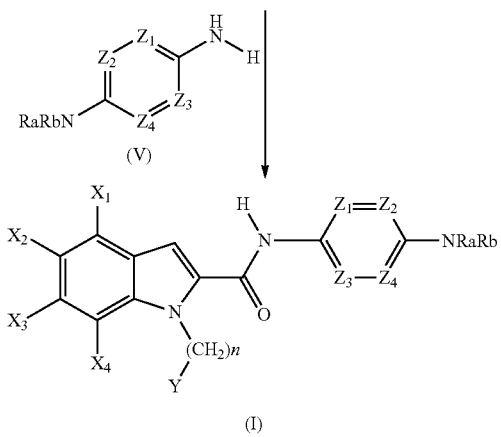

When the compound of general formula (III) is defined such that n is equal to 1, 2 or 3 and LG represents a leaving group such as a chlorine, bromine or iodine atom, the reaction can be carried out in the presence of a base, such as sodium hydride or potassium carbonate, in a polar solvent, such as dimethylformamide, dimethyl sulfoxide or acetone (n=1: Kolasa T., *Bioorg. Med. Chem.*, 1997, 5(3), 507, n=2: Abramovitch R., *Synth. Commun.*, 1995, 25(1), 1). When the compound of general formula (III) is defined such that n is equal to 1, 2 or 3 and LG represents a hydroxyl group, the compounds of general formula (IV) can be obtained by reaction of the compound of general formula (II) with a compound of general formula (III) in the presence of a phosphine, such as, for example, triphenylphosphine, and of a reactant, such as, for example, diethyl azodicarboxylate, in solution in a solvent, such as dichloromethane or tetrahydrofuran (O. Mitsonobu, *Synthesis*, 1981, 1-28).

When the compound of general formula (III) is defined such that n is equal to 0 and LG represents a leaving group such as a chlorine, bromine or iodine atom, the reaction can be carried out at a temperature of between 80° C. and 250° C. in the presence of a copper-based catalyst, such as copper bromide or copper oxide, and of a base, such as potassium carbonate (Murakami Y., *Chem. Pharm. Bull.,* 1995, 43(8), 1281). It is also possible to use the milder conditions described in S. L. Buchwald, *J. Am. Chem. Soc.,* 2002, 124, 11684.

The compound of general formula (IV) for which B represents a $C_1$-$C_6$-alkoxyl group can be converted to the compound of general formula (IV) where B represents a hydroxyl group by the action of a base, such as sodium hydroxide or potassium hydroxide, in solution in a solvent, such as ethanol. The compound of general formula (IV) where B represents a hydroxyl group can subsequently be converted to the compound of general formula (IV) where B represents a chlorine atom by the action of a chlorinating agent, such as thionyl chloride, in a solvent, such as dichloromethane.

The compound of general formula (I) can subsequently be obtained, for example, by reaction of a compound of general formula (IV) where B is a chlorine atom, as obtained above, with an amine of general formula (V), in which $Z_1$, $Z_2$, $Z_3$, $Z_4$, Ra and Rb are as defined in the general formula (I), in a solvent, such as dichloroethane, toluene or tetrahydrofuran.

The compound of general formula (I) can also be obtained by reaction of a compound of general formula (IV) where B is a hydroxyl group, as obtained above, with an amine of general formula (V), in which $Z_1$, $Z_2$, $Z_3$, $Z_4$, Ra and Rb are as defined in the general formula (I) in the presence of a coupling agent, such as diethyl cyanophosphonate, in the presence of a base, such as triethylamine, in a solvent, such as dimethylformamide.

The compounds of general formulae (I), (II) and (IV) in which $X_1$, $X_2$, $X_3$ and/or $X_4$ represent a cyano group or an aryl can be obtained by a coupling reaction, catalyzed by a metal, such as palladium, carried out on the corresponding compounds of general formulae (I), (II) and (IV) in which $X_1$, $X_2$, $X_3$ and/or $X_4$ represent a leaving group, for example a bromine, according to methods which are described in the literature or which are known to a person skilled in the art.

The compounds of general formulae (I), (II) and (IV) in which $X_1$, $X_2$, $X_3$ and/or $X_4$ represent a $C(O)NR_1R_2$ group can be obtained from the corresponding compounds of general formulae (I), (II) and (IV) in which $X_1$, $X_2$, $X_3$ and/or $X_4$ represent a cyano group according to methods which are described in the literature or which are known to a person skilled in the art.

The compounds of general formulae (I), (II) and (IV) in which $X_1$, $X_2$ r $X_3$, $X_4$ and/or $R_6$ correspond to an $-S(O)$-alkyl or $-S(O)_2$-alkyl group can be obtained by oxidation of the corresponding compounds of general formulae (I), (II) and (IV) in which $X_1$, $X_2$, $X_3$, $X_4$ and/or $R_6$ represent a $C_1$-$C_6$-thioalkyl group according to methods which are described in the literature or which are known to a person skilled in the art.

Likewise, the compounds of general formulae (I) and (IV) in which Y is substituted by an $-S(O)$-alkyl or $-S(O)_2$-alkyl group can be obtained by oxidation of the corresponding compounds of general formulae (I) and (IV) in which Y is substituted by a $C_1$-$C_6$-thioalkyl group according to methods which are described in the literature or which are known to a person skilled in the art.

The compounds of general formula (I) in which $Z_1$, $Z_2$, $Z_3$ and/or $Z_4$ represent a $C(R_6)$ group where $R_6$ represents a hydroxyl group can be obtained from the corresponding compounds of general formula (I) in which $Z_1$, $Z_2$, $Z_3$ and/or $Z_4$ represent a $C(R_6)$ group where $R_6$ represents a $C_1$-$C_6$-alkoxyl group according to methods which are described in the literature or which are known to a person skilled in the art.

The compounds of general formulae (I), (II) and (IV) in which $X_1$, $X_2$, $X_3$ and/or $X_4$ represent an $NR_1R_2$, $NR_3COR_4$ or $NR_3SO_2R_5$ group can be obtained from the corresponding compounds of general formulae (I), (II) and (IV) in which $X_1$, $X_2$, $X_3$ and/or $X_4$ represent a nitro group, for example by reduction and then acylation or sulfonylation, according to methods which are described in the literature or which are known to a person skilled in the art.

The compounds of general formulae (I), (II) and (IV) in which $X_1$, $X_2$, $X_3$ and/or $X_4$ represent an $NR_1R_2$, $NR_3COR_4$ or $NR_3SO_2R_5$ group can be obtained from the corresponding compounds of general formulae (I), (II) and (IV) in which $X_1$, $X_2$, $X_3$ and/or $X_4$ represent, for example, a bromine atom by a coupling reaction respectively with an amine, an amide or a sulfonamide in the presence of a base, of a phosphine and of a palladium-based catalyst according to methods which are described in the literature or which are known to a person skilled in the art.

The compounds of general formulae (I), (II) and (IV) in which $X_1$, $X_2$, $X_3$ and/or $X_4$ represent an $SO_2NR_1R_2$ group can be obtained by a method analogous to that described in *Pharmazie,* 1990, 45, 346, or according to methods which are described in the literature or which are known to a person skilled in the art.

The compound of general formula (I) in which NRaRb corresponds to an $NH_2$ group can be obtained, according to conditions known to a person skilled in the art and described in the literature (Greene and Wuts, *Protective Groups in Organic Synthesis,* Wiley-Interscience), from precursors of general formula (I) where NRaRb=NH-PG, PG corresponding to a protective group, such as an acetyl or tert-butoxycarbonyl group.

The compounds of general formula (III) are commercially available, are described in the literature (Carling R. W. et al., *J. Med. Chem.,* 2004 (47), 1807-1822, or Russel M. G. N. et al., *J. Med. Chem.,* 2005 (48), 1367-1383) or are accessible using methods known to a person skilled in the art. Some compounds of general formula (IV) are described in the literature (for example WO2007/010144). The compounds (V) and the other reactants, when their method of preparation is not described, are commercially available or are described in the literature (for example WO05028452, WO02048152, WO06040522, WO004052869, WO004/062665, JP540028330, GB 870 027, U.S. Pat. No. 4,104,385, WO004110985, *Heterocycles,* 1977, 6(12), 1999-2004).

The invention, according to another of its aspects, also has as subject matter the compounds of general formulae (Va) and (Vb). These compounds are of use as intermediates in the synthesis of the compounds of formula (I).

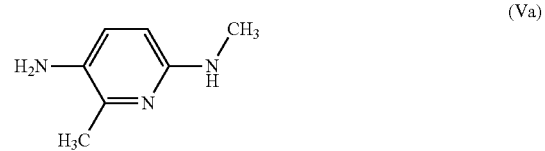

(Va)

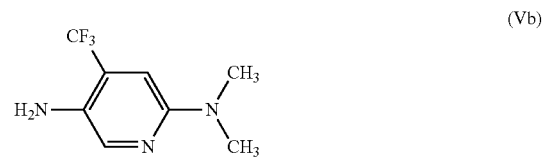

(Vb)

The amines Va and Vb are prepared according to the processes described in examples Nos. 8 and 10.

The following examples describe the preparation of some compounds in accordance with the invention. These examples are not limiting and serve only to illustrate the present invention. The numbers of the compounds exemplified refer to those given in table 1. The elemental microanalyses, the LC-MS (liquid chromatography coupled to mass spectrometry) analyses, the IR spectra and the NMR spectra confirm the structures of the compounds obtained.

EXAMPLE 1

Compound No. 1

N-[6-(Methylamino)pyridin-3-yl]-5-fluoro-1-(3-fluorobenzyl)-1H-indole-2-carboxamide

1.1
5-Fluoro-1-(3-fluorobenzyl)-1H-indole-2-carboxylic acid

An aqueous sodium hydroxide solution, prepared from 1.15 g (28.92 mmol) of sodium hydroxide pellets in 50 ml of water, is added to a solution of 7.6 g (24.10 mmol) of ethyl 5-fluoro-1-(3-fluorobenzyl)-1H-indole-2-carboxylate (WO2006/024776) in 241 ml of ethanol. The mixture is heated for two hours and then concentrated under reduced pressure. The resulting solid is taken up in 200 ml of water. The solution is washed with two times 100 ml of ethyl ether, acidified by successive additions of small amounts of concentrated hydrochloric acid and then extracted with 200 ml of ethyl acetate. The organic phase is finally washed twice with 100 ml of water and once with 50 ml of a saturated sodium chloride solution, dried over magnesium sulfate and concentrated under reduced pressure. After drying at 50° C. under reduced pressure, 6.4 g of the expected product are obtained in the form of a solid which will be used as is in the following stage.

1.2 N-[6-(Methylamino)pyridin-3-yl]-5-fluoro-1-(3-fluorobenzyl)-1H-indole-2-carboxamide

Compound No. 1

0.27 ml (1.67 mmol) of diethyl cyanophosphonate is added dropwise at 20° C. under argon to a solution of 0.4 g (1.39 mmol) of 5-fluoro-1-(3-fluorobenzyl)-1H-indole-2-carboxylic acid (obtained in step 1.1) and 0.216 g (1.67 mmol) of 3-amino-6-(methylamino)pyridine (WO2005/028452) in 10 ml of dry dimethylformamide. The mixture is stirred for 10 minutes and then 0.43 ml (3.08 mmol) of triethylamine is added dropwise. The mixture is stirred at ambient temperature for 18 hours and concentrated under reduced pressure, and then the residue is taken up in 50 ml of ethyl acetate. This solution is then successively washed with three times ml of a saturated sodium hydrogencarbonate solution, 50 ml of water and 20 ml of a saturated sodium chloride solution and then dried over sodium sulfate, filtered and concentrated under reduced pressure. The solid obtained is triturated from hot isopropyl ether. 0.471 g of a solid is obtained, which solid is dried under reduced pressure.

Melting point: 225-227° C.
$^1$H NMR ($d_6$-DMSO), δ (ppm): 2.61 (d, 3H); 5.82 (s, 2H); 6.3 (q, 1H); 6.41 (d, 1H); 7.02 (m, 6H); 7.49 (m, 2H); 7.65 (d×d, 1H); 8.2 (d, 1H); 10.15 (s, 1H)

EXAMPLE 2

Compound No. 2

N-[6-(Dimethylamino)pyridin-3-yl]-5-fluoro-1-(3-fluorobenzyl)-1H-indole-2-carboxamide hydrochloride (1:1)

2.1 N-[6-(Dimethylamino)pyridin-3-yl]-5-fluoro-1-(3-fluorobenzyl)-1H-indole-2-carboxamide 0.27 ml (1.67 mmol) of diethyl cyanophosphonate is added dropwise at 20° C. under argon to a solution of 0.4 g (1.39 mmol) of 5-fluoro-1-(3-fluorobenzyl)-1H-indole-2-carboxylic acid (obtained in Example 1.1) and 0.229 g (1.67 mmol) of 3-amino-6-(dimethylamino)pyridine in 3.5 ml of dry dimethylformamide. The mixture is stirred for 10 minutes and then 0.43 ml (3.06 mmol) of triethylamine is added dropwise. The mixture is stirred at ambient temperature for 18 hours and concentrated under reduced pressure, and then the residue is taken up in 50 ml of ethyl acetate. This solution is then successively washed with three times 20 ml of a saturated sodium hydrogencarbonate solution, 50 ml of water and 20 ml of a saturated sodium chloride solution and then dried over sodium sulfate, filtered and concentrated under reduced pressure. The solid obtained is triturated from hot isopropyl ether. 0.423 g of a solid is collected by filtration, which solid is dried under reduced pressure and used as in the following stage.

2.2 N-[6-(Dimethylamino)pyridin-3-yl]-5-fluoro-1-(3-fluorobenzyl)-1H-indole-2-carboxamide hydrochloride (1:1) Compound No. 2

A suspension of the solid obtained in stage 2.1 in isopropyl ether and a 4N solution of hydrochloric acid in dioxane is stirred at 0° C. The solid is collected by filtration, dried, again triturated from hot isopropyl ether, collected by filtration and dried under reduced pressure.

Melting point: 232-234° C.; HCl (1:1)
$^1$H NMR ($d_6$-DMSO), δ (ppm): 3.2 (s, 6H); 5.85 (s, 2H); 6.80 (m, 2H); 7.0 (m, 1H); 7.2 (m, 3H); 7.5 (m, 3H); 8.2 (d, 1H); 8.5 (s, 1H); 10.85 (s, 1H).

EXAMPLE 3

Compound No. 12

N-[6-(Dimethylamino)pyridin-3-yl]-5-trifluoromethyl-1-(3-fluorobenzyl)-1H-indole-2-carboxamide 0.185 g (1.35 mmol) of 3-amino-6-(dimethylamino)pyridine (WO2005/028452) in 2 ml of dry dimethylformamide is added dropwise at 20° C. under argon to a solution of 0.35 g (1.04 mmol) of 5-trifluoromethyl-1-(3-fluorobenzyl)-1H-indole-2-carboxylic acid (WO2006/072736), 0.198 g (1.14 mmol) of N-(3-dimethylaminopropyl)-N'-ethylcarbodiimide hydrochloride and 0.165 g (1.14 mmol) of 1-hydroxybenzotriazole monohydrate in 6 ml of dry dimethylformamide. The reaction mixture is stirred overnight, run onto 100 ml of water and then extracted three times with 50 ml of ethyl acetate. The organic phases are subsequently combined, washed three times with 20 ml of water, dried over sodium sulfate and then concentrated under reduced pressure. The expected product is purified by chromatography on a silica column, elution being carried out with a mixture of dichloromethane and methanol. 0.19 g of the expected compound is thus isolated.

Melting point: 192-193° C.
$^1$H NMR ($d_6$-DMSO), δ (ppm): 3.01 (s, 6H); 5.93 (s, 2H); 6.68 (d, 1H); 6.92 (m, 2H); 7.06 (t×d, 1H); 7.32 (m, 1H); 7.51 (s, 1H); 7.58 (d, 1H); 7.78 (d, 1H); 7.85 (d, 1H); 8.2 (s, 1H); 8.39 (s, 1H); 10.39 (s, 1H).

EXAMPLE 4

Compound No. 16

N-[6-(Dimethylamino)-5-methylpyridin-3-yl]-5-fluoro-1-(3-fluorobenzyl)-1H-indole-2-carboxamide Compound No. 16 is prepared from 5-fluoro-1-(3-fluorobenzyl)-1H-indole-2-carboxylic acid (WO2006/072736)

and 3-amino-5-methyl-6-dimethylaminopyridine (GB 870 027) according to a process similar to that described in example No. 3.

Melting point: 145-146° C.

$^1$H NMR (d$_6$-DMSO), δ (ppm): 2.28 (s, 3H); 2.78 (s, 6H); 5.91 (s, 2H); 6.91 (m, 2H); 7.06 (t×d, 1H); 7.26 (t×d, 1H); 7.31 (m, 1H); 7.41 (s, 1H); 7.58 (m, 2H); 7.88 (s, 1H); 8.39 (s, 1H); 10.39 (s, 1H).

EXAMPLE 5

Compound No. 19

N-[6-(Dimethylamino)-5-methylpyridin-3-yl]-5-fluoro-1-(pyridin-4-ylmethyl)-1H-indole-2-carboxamide 5.1 5-Fluoro-1-(pyridin-4-ylmethyl)-1H-indole-2-carboxylic acid A solution of 2.1 g (7.04 mmol) of ethyl 5-fluoro-1-(pyridin-4-ylmethyl)-1H-indole-2-carboxylate and 1.18 g (21.12 mmol) of potassium hydroxide in 80 ml of ethanol and 2 ml of water is heated at reflux for 2 hours. The reaction mixture is subsequently concentrated under reduced pressure. 100 ml of water are added and the pH of the solution is brought to pH 8 by addition of a concentrated hydrochloric acid solution. A precipitate is collected by filtration and is washed with water and then dried under reduced pressure. 1.5 g of the expected product are thus obtained.

Melting point: 282-283° C.

5.2 N-[6-(Dimethylamino)-5-methylpyridin-3-yl]-5-fluoro-1-(pyridin-4-ylmethyl)-1H-indole-2-carboxamide (Compound No. 19)

Compound No. 19 is prepared from 5-fluoro-1-(pyridin-4-ylmethyl)-1H-indole-2-carboxylic acid, synthesized in stage 5.1, and 3-amino-5-methyl-6-(dimethylamino)pyridine (GB 870 027) according to a process similar to that described in example No. 3.

Melting point: 164-165° C.

$^1$H NMR (d$_6$-DMSO), δ (ppm): 2.28 (s, 3H); 2.75 (s, 6H); 5.91 (s, 2H); 6.99 (d, 2H); 7.26 (t×d, 1H); 7.46 (s, 1H); 7.58 (m, 2H); 7.85 (s, 1H); 8.36 (s, 1H); 8.49 (d, 2H); 10.39 (s, 1H).

EXAMPLE 6

Compound No. 20

N-[6-(Dimethylamino)-5-(trifluoromethyl)pyridin-3-yl]-5-fluoro-1-(3-fluorobenzyl)-1H-indole-2-carboxamide Compound No. 20 is prepared from 5-fluoro-1-(3-fluorobenzyl)-1H-indole-2-carboxylic acid (WO2006/072736) and 3-amino-5-trifluoromethyl-6-(dimethylamino)pyridine according to a process similar to that described in example No. 3.

Melting point: 142-143° C.

$^1$H NMR (d$_6$-DMSO), δ (ppm): 2.89 (s, 6H); 5.89 (s, 2H); 6.88 (m, 2H); 7.03 (t×d, 1H); 7.15 (t×d, 1H); 7.31 (m, 1H); 7.42 (s, 1H); 7.59 (m, 2H); 8.4 (s, 1H); 8.72 (s, 1H); 10.65 (s, 1H).

EXAMPLE 7

Compound No. 11

N-[6-(Acetylamino)pyridin-3-yl]-5-fluoro-1-(3-fluorobenzyl)-1H-indole-2-carboxamide Compound No. 11 is prepared from 5-fluoro-1-(3-fluorobenzyl)-1H-indole-2-carboxylic acid (WO2006/072736) and 6-acetylamino-3-aminopyridine according to a process similar to that described in example No. 3.

Melting point: 252-254° C.

$^1$H NMR (de-DMSO), δ (ppm): 2.08 (s, 3H); 5.89 (s, 2H); 6.89 (m, 2H); 7.01 (t×d, 1H); 7.15 (t×d, 1H); 7.29 (m, 1H); 7.41 (s, 1H); 7.58 (m, 2H); 8.06 (s, 2H); 8.68 (s, 1H); 10.42 (s, 1H); 10.56 (s, 1H).

EXAMPLE 8

Compound No. 21

N-[6-Methylamino-2-methylpyridin-3-yl]-5-fluoro-1-(3-fluorobenzyl)-1H-indole-2-carboxamide 8.1 6-Methylamino-2-methyl-3-aminopyridine (Compound No. Va)

A suspension of 0.4 g (2.39 mmol) of 6-methylamino-2-methyl-3-nitropyridine (Prace Naukowe Akedimii Ekonomicznej imienia Oskara Langego we Wroclawiu (1988), 435, 119-28) and 0.1 g of 10% palladium-on-charcoal in 50 ml of methanol is stirred at 20° C. for 6 hours under 4 atmospheres of hydrogen. The reaction mixture is subsequently filtered through a celite plug and then concentrated under reduced pressure. 0.33 g of the expected product is thus isolated in the form of an oil which will be used as is in the continuation of the synthesis.

8.2 N-[6-Methylamino-2-methylpyridin-3-yl]-5-fluoro-1-(3-fluorobenzyl)-1H-indole-2-carboxamide (Compound No. 21)

Compound No. 21 is prepared from 5-fluoro-1-(3-fluorobenzyl)-1H-indole-2-carboxylic acid (WO2006/072736) and 6-methylamino-2-methyl-3-aminopyridine (Va), prepared in stage 8.1, according to a process similar to that described in example no. 3.

Melting point: 229-230° C.

$^1$H NMR (d$_6$-DMSO), δ (ppm): 2.18 (s, 3H); 2.75 (s, 3H); 5.86 (s, 2H); 6.26 (d, 1H); 6.36 (m, 1H); 6.85 (d, 1H); 6.91 (d, 1H); 7.03 (t×d, 1H); 7.13 (t×d, 1H); 7.22 (d, 1H); 7.31 (m, 1H); 7.35 (s, 1H); 7.51 (d×d, 1H); 7.6 (m, 1H); 9.9 (s, 1H).

EXAMPLE 9

Compound No. 27

N-[6-Dimethylamino-5-fluoropyridin-3-yl]-5-fluoro-1-(3-fluorobenzyl)-1H-indole-2-carboxamide Compound No. 27 is prepared from 0.3 g (1.04 mmol) of 5-fluoro-1-(3-fluorobenzyl)-1H-indole-2-carboxylic acid (WO2006/072736) and 0.3 g (1.57 mmol) of 6-dimethylamino-5-fluoro-3-aminopyridine hydrochloride (WO2004/110986) according to a process similar to that described in example No. 3.

Melting point: 158-159° C.

$^1$H NMR (d$_6$-DMSO), δ (ppm): 3.11 (s, 6H); 5.89 (s, 2H); 6.8 (d×t, 1H); 6.97 (m, 2H); 7.12 (m, 2H); 7.35 (m, 3H); 7.91 (m, 3H).

EXAMPLE 10

Compound No. 28

N-[6-Dimethylamino-4-(trifluoromethyl)pyridin-3-yl]-5-fluoro-1-(3-fluorobenzyl)-1H-indole-2-carboxamide 10.1 Methyl 6-dimethylamino-4-(trifluoromethyl)-pyridine-3-carboxylate A mixture of 2.5 g (10.43 mmol) of methyl 6-chloro-4-(trifluoromethyl)nicotinate and 18.4 ml (146 mmol) of a 40% solution of dimethylamine in water is heated at 100° C. for 1 hour. A precipitate is subsequently collected by filtering the cooled mixture and is washed with 150 ml of water. After drying under reduced pressure, 2.3 g of the expected compound are isolated.

$^1$H NMR (CDCl$_3$), δ (ppm): 3.27 (s, 6H); 3.94 (s, 3H); 6.81 (s, 1H); 8.9 (s, 1H).

10.2 6-Dimethylamino-4-(trifluoromethyl)pyridine-3-carboxylic acid

A mixture of 2.3 g (9.27 mmol) of methyl 6-dimethylamino-4-(trifluoromethyl)pyridine-3-carboxylate, obtained in stage 10.1, and 0.78 g (13.9 mmol) of potassium hydroxide in 50 ml of methanol and 2 ml of water is stirred at 20° C. for 24 hours. The mixture is subsequently concentrated under reduced pressure. 100 ml of water are subsequently added and the solution is washed with 100 ml of dichloromethane and then acidified to pH 4 by addition of concentrated hydrochloric acid. A precipitate is collected by filtration and is washed with 50 ml of water. After drying under reduced pressure, 1.7 g of the expected compound are isolated.

$^1$H NMR (d$_6$-DMSO), δ (ppm): 3.19 (s, 6H); 6.9 (s, 1H); 8.75 (s, 1H); 12.87 (broad peak, 1H).

10.3 6-Dimethylamino-4-trifluoromethyl-3-(tert-butoxycarbonylamino)pyridine

A mixture of 1.7 g (7.26 mmol) of 6-dimethylamino-4-(trifluoromethyl)pyridine-3-carboxylic acid, obtained in stage 10.2, 2.03 ml (9.44 mmol) of diphenyl phosphoryl azide and 2.53 ml (18.15 mmol) of triethylamine in 23 ml of tert-butanol is heated at 90° C. for 5 hours. The reaction mixture is subsequently concentrated under reduced pressure and the residue is taken up in 50 ml of water and extracted 3 times with 50 ml of dichloromethane. The organic phases are combined, washed with 50 ml of water, dried over sodium sulfate and then concentrated under reduced pressure. The oil obtained is purified by chromatography on a silica column, elution being carried out with a mixture of dichloromethane and methanol. 0.75 g of the expected product is thus isolated.

$^1$H NMR (CDCl$_3$), δ (ppm): 1.39 (s, 9H); 3.07 (s, 6H); 5.91 (broad peak, 1H); 6.53 (s, 1H); 8.31 (s, 1H).

10.4 6-Dimethylamino-4-trifluoromethyl-3-aminopyridine hydrochloride

Amine Vb

A solution of 0.73 g (2.39 mmol) of 6-dimethylamino-4-trifluoromethyl-3-(tert-butoxycarbonylamino)pyridine, prepared in stage 10.3, in 8.5 ml of 4N hydrochloric acid in dioxane is stirred at reflux for 5 hours. 200 ml of ethyl ether are subsequently added to the cooled reaction mixture. 0.6 g of a precipitate is collected by filtration.

Melting point: 198-201° C.

$^1$H NMR (d$_6$-DMSO), δ (ppm): 3.11 (s, 6H); 7.2 (s, 1H); 7.21 (broad peak, 2H); 8.09 (s, 1H).

10.5 N-[6-dimethylamino-4-(trifluoromethyl)pyridin-3-yl]-5-fluoro-1-(3-fluorobenzyl)-1H-indole-2-carboxamide Compound No. 28

Compound No. 28 is prepared from 0.3 g (1.04 mmol) of 5-fluoro-1-(3-fluorobenzyl)-1H-indole-2-carboxylic acid (WO2006/072736) and 0.328 g (1.36 mmol) of 6-dimethylamino-4-trifluoromethyl-3-aminopyridine hydrochloride, described in stage 10.4, according to a process similar to that described in example No. 3.

Melting point: 209-210° C.

$^1$H NMR (CDCl$_3$), δ (ppm): 3.2 (s, 6H); 5.86 (s, 2H); 6.75 (s, 1H); 6.82 (m, 1H); 6.98 (m, 2H); 7.12 (m, 2H); 7.3 (m, 2H); 7.41 (m, 1H); 7.66 (s, 1H); 8.61 (m, 1H).

The chemical structures and the physical properties of some compounds of general formula (I) according to the invention are illustrated in the following table 1.

In this table:
- the "M.p." column gives the melting points of the products in degrees Celsius (° C.);
- in the "Salt/Base" column, "-" represents a compound in the form of the free base, whereas "HCl" represents a compound in the hydrochloride form and the ratio in brackets is the base:acid ratio;
- "nPr" represents a linear propyl chain, "cycloPr" represents a cyclopropyl group and "Ac" represents an acetyl group.

TABLE 1

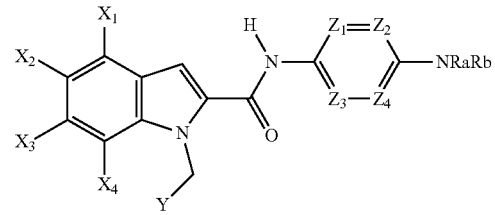

(I)

| No. | X$_1$, X$_2$, X$_3$, X$_4$ | Y | Z$_1$, Z$_2$, Z$_3$, Z$_4$ | NR$_a$R$_b$ | M.p. (° C.) | Salt/Base |
|---|---|---|---|---|---|---|
| 1 | H, F, H, H | 3-fluorophenyl | CH, CH, CH, N | NHCH$_3$ | 225-227 | — |
| 2 | H, F, H, H | 3-fluorophenyl | CH, CH, CH, N | N(CH$_3$)$_2$ | 232-234 | HCl (1:1) |
| 3 | H, F, H, H | phenyl | CH, CH, CH, N | NHCH$_3$ | 246-247 | — |
| 4 | H, F, H, H | phenyl | CH, CH, CH, N | N(CH$_3$)$_2$ | 196-197 | — |
| 5 | H, H, F, H | 3-fluorophenyl | CH, CH, CH, N | N(CH$_3$)$_2$ | 194-195 | — |
| 6 | H, F, H, H | 3-fluorophenyl | CH, CH, N, CH | N(CH$_3$)$_2$ | 190-192 | — |
| 7 | H, F, H, H | 2-fluorophenyl | CH, CH, CH, N | NHCH$_3$ | 253-254 | — |
| 8 | H, F, H, H | 3-fluorophenyl | CH, CH, CH, N | NHnPr | 132-134 | HCl (1:1) |
| 9 | H, F, H, H | 3-fluorophenyl | CH, CH, CH, N | NHcycloPr | 120-140 | HCl (1:1) |
| 10 | H, F, H, H | 4-fluorophenyl | CH, CH, CH, N | N(CH$_3$)$_2$ | 208-209 | — |
|  |  |  |  |  | 228-229 | HCl (1:1) |
| 11 | H, F, H, H | 3-fluorophenyl | CH, CH, CH, N | NHAc | 252-254 | — |

TABLE 1-continued (I)

| No. | $X_1, X_2, X_3, X_4$ | Y | $Z_1, Z_2, Z_3, Z_4$ | $NR_aR_b$ | M.p. (° C.) | Salt/Base |
|---|---|---|---|---|---|---|
| 12 | H, $CF_3$, H, H | 3-fluorophenyl | CH, CH, CH, N | $N(CH_3)_2$ | 192-193 | — |
| 13 | H, F, H, H | 3-fluorophenyl | C—$CH_3$, CH, CH, N | $N(CH_3)_2$ | 183-185 | — |
| 14 | H, H, $CF_3$, H | 3-fluorophenyl | CH, CH, CH, N | NHAc | 293-295 | — |
| 15 | H, F, H, H | 3-fluorophenyl | C—$CH_3$, CH, CH, N | $NHCH_3$ | 215-217 | — |
| 16 | H, F, H, H | 3-fluorophenyl | CH, C—$CH_3$, CH, N | $N(CH_3)_2$ | 145-146 | — |
| 17 | H, F, H, H | pyridin-4-yl | C—$CH_3$, CH, CH, N | $N(CH_3)_2$ | 217-219 | — |
| 18 | H, F, H, H | pyridin-4-yl | C—$CH_3$, CH, CH, N | $NHCH_3$ | 218-220 | — |
| 19 | H, F, H, H | pyridin-4-yl | CH, C—$CH_3$, CH, N | $N(CH_3)_2$ | 164-165 | — |
| 20 | H, F, H, H | 3-fluorophenyl | CH, C—$CF_3$, CH, N | $N(CH_3)_2$ | 142-143 | — |
| 21 | H, F, H, H | 3-fluorophenyl | CH, CH, C—$CH_3$, N | $NHCH_3$ | 229-230 | — |
| 22 | H, F, H, H | 3-fluorophenyl | CH, CH, N, N | $N(CH_3)_2$ | 239-241 169-170 | HCl (1:1) — |
| 23 | H, $CF_3$, H, H | 3-fluorophenyl | CH, CH, N, N | $N(CH_3)_2$ | 138-139 | — |
| 24 | H, H, $CF_3$, H | 3-fluorophenyl | CH, CH, N, N | $N(CH_3)_2$ | 255-267 | — |
| 25 | H, $CF_3$, H, H | pyridin-4-yl | CH, CH, N, N | $N(CH_3)_2$ | 269-272 | HCl (1:1) |
| 26 | H, F, H, H | pyridin-4-yl | CH, CH, CH, N | $NHCH_3$ | 220-222 | — |
| 27 | H, F, H, H | 3-fluorophenyl | CH, C—F, CH, N | $N(CH_3)_2$ | 158-159 | — |
| 28 | H, F, H, H | 3-fluorophenyl | C—$CF_2$, CH, CH, N | $N(CH_3)_2$ | 209-210 | — |

The compounds of the invention were subjected to in vitro and in vivo pharmacological assays which demonstrated their advantage as substances possessing therapeutic activities.

The compounds of the invention also exhibit characteristics of solubility in water which favor a good in vivo activity.

Test of the Inhibition of the Current Induced by Capsaicin with Regard to Rat DRGs Primary Culture of Rat Dorsal Root Ganglion (DRG) Cells:

The neurons of the DRG naturally express the TRPV1 receptor.

Primary cultures of DRGs of newborn rats are prepared from one-day-old rats. Briefly, after dissection, the ganglions are trypsinized and the cells dissociated mechanically by gentle trituration. The cells are resuspended in an Eagle's basal culture medium comprising 10% of fetal calf serum, 25 mM KCl, 2 mM glutamine, 100 µg/ml of gentamicin and 50 ng/ml of NGF and then deposited on glass cover slips covered with laminin (0.25×106 cells per cover slip) which are subsequently placed in 12-well Corning dishes. The cells are incubated at 37° C. in a humidified atmosphere comprising 5% of $CO_2$ and 95% of air. Cytosine β-D-arabinoside (1 µM) is added 48 h after culturing, in order to prevent the growth of non-neuronal cells. After culturing for 7-10 days, the cover slips are transferred into experimental chambers for the patch clamp studies.

Electrophysiology:

The measurement chambers (volume 800 µl) comprising the cell preparation are placed on the stage of an inverted microscope (Olympus IMT2) equipped with Hoffman optics (Modulation Contrast, New York) and are observed at a magnification of 400×. The chambers are continuously perfused by gravity (2.5 ml/min) using a distributor of solutions which has 8 inlets, the single outlet of which, composed of a polyethylene tube (opening 500 µm), is placed at least 3 mm from the cell studied. The "whole cell" configuration of the patch clamp technique was used. Borosilicate glass pipettes (resistance 5-10 Mohms) are brought close to the cell using a 3D piezoelectric micromanipulator (Burleigh, PC1000). The overall currents (membrane potential set at −60 mV) are recorded with an Axopatch 1D amplifier (Axon Instruments, Foster City, Calif.) connected to a PC controlled by Pclamp8 software (Axon Instruments). The current plots are recorded on paper and simultaneously recorded digitally (sampling frequency 15 to 25 Hz) and acquired on the hard disk of the PC.

The application of a micromolar capsaicin solution produces an incoming cationic current with regard to the DRG cells (voltage set at −70 mV). In order to minimize the desensitization of the receptors, a minimum interval of one minute between two applications of capsaicin is observed. After a control period (stabilization of the capsaicin alone response), the test compounds are applied alone at a given concentration (concentration of 10 nM or 0.1 nM) for a period of time of 4 to 5 minutes, during which several capsaicin+compound tests are carried out (obtaining the maximum inhibition). The results are expressed as % of inhibition of the control capsaicin response.

The percentages of inhibition of the capsaicin (1 microM) response are between 20% and 100% for the most active compounds of the invention tested at a concentration of 10 nM to 0.1 nM (see example in table 2).

The compounds of the invention are thus effective in vitro antagonists of receptors of TRPV1 type.

TABLE 2

| Compound No. | % Inhibition by the DRG patch technique |
|---|---|
| 1 | 53% (1 nM) |
| 12 | 100% (1 nM) |
| 17 | 60% (10 nM) |
| 19 | 33% (10 nM) |

Mouse Corneal Irritation Test

The irritating nature of capsaicin is easily assessed on the cornea since this organ is one of the most innervated by C fibers. In this context, according to preliminary experiments, the application of a very small amount of capsaicin (2 µl at a concentration of 160 µM) at the surface of the cornea of an animal results in a number of kinds of stereotyped behavior related to irritation which are easy to record. These include: blinking of the eye, rubbing of the instilled eye by the ipsilateral front paw, rubbing of the face with the two front paws and scratching of the ipsilateral face by the hind paw. The duration of these kinds of behavior does not exceed 2 minutes of observation and the animal then resumes its normal activity. Its appearance is furthermore also normal. The mouse does not hide in a corner with the hairs standing on end and does not develop any observable signs of suffering. It may be concluded therefrom that the duration of action of capsaicin at these doses is less than 2 minutes.

Summary of the Methodology:

The principle of the series of experiments is to determine whether the compounds of the invention can influence the behavioral response induced by a given amount of capsaicin. Capsaicin is initially diluted to 25 mM in DMSO and is diluted, for its final use, in physiological saline with 10% Tween 80. It appears, from control studies, that the solvent has no effect under these conditions.

In practice, the test product, prepared at 25 mM in DMSO and diluted for its final use in physiological saline with 10% Tween 80 to the stronger concentration of 500 µM, is administered in local application at the surface of the cornea under a volume of 2 µl, 10 minutes before the application of the capsaicin. The animal receives the ocular instillation of 2 µl of a 160 µM capsaicin solution prepared as indicated above. During observation for 2 minutes following the instillation, the number of rubbing actions on the instilled eye by the ipsilateral front paw is counted for each animal.

For a given group, the percentage of protection is calculated as follows:

$P=100-((\text{mean number of scratching actions of the group treated with the compound/mean number of scratching actions of the group treated with the solvent}) \times 100)$.

This percentage of protection is converted to a mean for each group of animals (n=number of animals tested with the compound of the invention).

The percentages of protection evaluated in this model for the most active compounds of the invention, used at a concentration of 500 µM, are between 20% and 100% (see example in table 3):

TABLE 3

| Compound No. | % P (500 µM) |
|---|---|
| 1 | 23% |

The results of these trials show that the most active compounds of the invention block the effects induced by the stimulation of the TRPV1 receptors.

The compounds of the invention can thus be used for the preparation of medicaments, in particular for the preparation of a medicament intended to prevent or to treat pathologies in which receptors of TRPV1 type are involved.

Thus, according to another of its aspects, a subject matter of the invention is medicaments which comprise a compound of formula (I) or a pharmaceutically acceptable salt or also a hydrate or a solvate of said compound.

These medicaments are employed in therapeutics, in particular in the prevention and/or the treatment of pain and inflammation, chronic, neuropathic (traumatic, diabetic, metabolic, infectious, toxic, induced by an anticancer treatment or iatrogenic), (osteo)arthritic or rheumatic pain, fibromyalgia, bone pain, cancer-related pain, trigeminal neuralgia, cephalgia, migraine, dental pain, burns, sunburn, bites or stings, post-herpetic neuralgia, muscle pain, nerve compression (central and/or peripheral), marrow and/or brain trauma, ischemia (of the marrow and/or brain), neurodegeneration, hemorrhagic vascular accidents (of the marrow and/or brain) or post-stroke pain.

The compounds of the invention can be used for the preparation of a medicament intended to prevent and/or to treat urological disorders, such as bladder hyperactivity, bladder hyperreflexia, bladder instability, incontinence, urgent urination, urinary incontinence, cystitis, renal colic, pelvic hypersensitivity and pelvic pain.

The compounds of the invention can be used for the preparation of a medicament intended to prevent and/or to treat gynecological disorders, such as vulvodynia, salpingitis-related pain or dysmenorrhea.

These products can also be used for the preparation of a medicament intended to prevent and/or to treat gastrointestinal disorders, such as gastro-esophageal reflux disorder, stomach ulcers, duodenal ulcers, functional dyspepsia, colitis, IBS, Crohn's disease, pancreatitis, esophagitis or biliary colic.

The compounds of the invention can also be used for the preparation of a medicament intended to treat diabetes. Likewise, the products of the present invention may be of use in the prevention and/or the treatment of respiratory disorders, such as asthma, coughs, COPD, bronchoconstriction and inflammatory disorders. These products can also be used to prevent and/or to treat psoriasis, pruritus, irritation of the skin, eyes or mucous membranes, herpes or shingles.

The compounds of the invention can also be used for the preparation of a medicament intended to treat depression.

According to another of its aspects, the present invention relates to pharmaceutical compositions comprising, as active principle, a compound according to the invention. These pharmaceutical compositions comprise an effective dose of at least one compound according to the invention, or a pharmaceutically acceptable salt, a hydrate or a solvate of said compound, and at least one pharmaceutically acceptable excipient.

Said excipients are chosen, according to the pharmaceutical form and the method of administration desired, from the usual excipients known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in unit administration form, as a mixture with conventional pharmaceutical excipients, to animals and human beings for the prophylaxis or the treatment of the disorders or diseases mentioned above.

The appropriate unit administration forms comprise oral forms, such as tablets, soft or hard gelatin capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. The compounds according to the invention can be used, for topical application, in creams, gels, ointments or lotions.

By way of example, a unit administration form of a compound according to the invention in the tablet form can comprise the following components:

| | |
|---|---:|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

Said unit forms comprise doses in order to make possible daily administration of 0.001 to 30 mg of active principle per kg of body weight, depending on the pharmaceutical dosage form.

There may be specific cases where higher or lower dosages are appropriate; such dosages do not depart from the scope of the invention. According to the usual practice, the dosage appropriate to each patient is determined by the physician according to the method of administration and the weight and response of said patient.

The present invention, according to another of its aspects, also relates to a method for the treatment of the pathologies indicated above which comprises the administration, to a patient, of an effective dose of a compound according to the invention, or one of its pharmaceutically acceptable salts or hydrates or solvates.

What is claimed is:

1. A compound of formula (Vb):

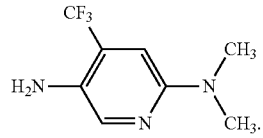

(Vb)

* * * * *